(12) United States Patent
Boon et al.

(10) Patent No.: US 10,106,746 B2
(45) Date of Patent: Oct. 23, 2018

(54) METHODS AND SYSTEMS FOR SUPPLYING HYDROGEN TO A HYDROCATALYTIC REACTION

(71) Applicant: SHELL OIL COMPANY, Houston, TX (US)

(72) Inventors: Andries Quirin Maria Boon, Houston, TX (US); Joseph Broun Powell, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 15/832,805

(22) Filed: Dec. 6, 2017

(65) Prior Publication Data

US 2018/0163141 A1    Jun. 14, 2018

Related U.S. Application Data

(60) Provisional application No. 62/431,452, filed on Dec. 8, 2016.

(51) Int. Cl.

| | | |
|---|---|---|
| *C10G 1/06* | (2006.01) | |
| *C01B 3/38* | (2006.01) | |
| *C10G 3/00* | (2006.01) | |
| *C12P 5/02* | (2006.01) | |
| *G06Q 30/00* | (2012.01) | |
| *C12M 1/00* | (2006.01) | |

(52) U.S. Cl.
CPC ............... *C10G 1/06* (2013.01); *C01B 3/38* (2013.01); *C10G 3/42* (2013.01); *C12M 43/00* (2013.01); *C12P 5/023* (2013.01); *G06Q 30/018* (2013.01); *C01B 2203/0233* (2013.01); *C01B 2203/0244* (2013.01); *C10G 2300/1011* (2013.01); *C10G 2300/202* (2013.01)

(58) Field of Classification Search
CPC .. C10G 2300/1014; C10G 3/42; C10G 1/065; C10G 3/50; C10G 2300/1011; C10G 3/00; C10G 2300/44; C07C 29/132; C07C 29/60; C07C 1/24
See application file for complete search history.

(56) References Cited

U.S. PATENT DOCUMENTS

| | | | |
|---|---|---|---|
| 9,174,898 B2* | 11/2015 | Komplin | ............... C07C 29/132 |
| 9,222,028 B2* | 12/2015 | Powell | ................. C07G 1/00 |
| 9,938,466 B2* | 4/2018 | Linck | .................. C10G 1/002 |
| 2010/0251615 A1* | 10/2010 | Marker | .................. C01B 3/16 |
| | | | 48/127.7 |

* cited by examiner

*Primary Examiner* — Sharon Pregler

(57) ABSTRACT

Systems and methods involving hydrocatalytic reactions that use molecular hydrogen obtained from a biogas generated from at least a portion of the hydrocatalytic reaction product. Hydrocatalytic reactions can require significant quantities of molecular hydrogen, particularly if the molecular hydrogen is being introduced under dynamic flow conditions. The present disclosure provides systems and methods that can allow for reducing the carbon footprint of the fuels formed from the hydrocatalytic reaction because at least a portion of the hydrogen used in the hydrocatalytic reaction has low carbon footprint. A fuel with low carbon footprint can qualify for certain governmental status that provides certain benefits.

13 Claims, 1 Drawing Sheet

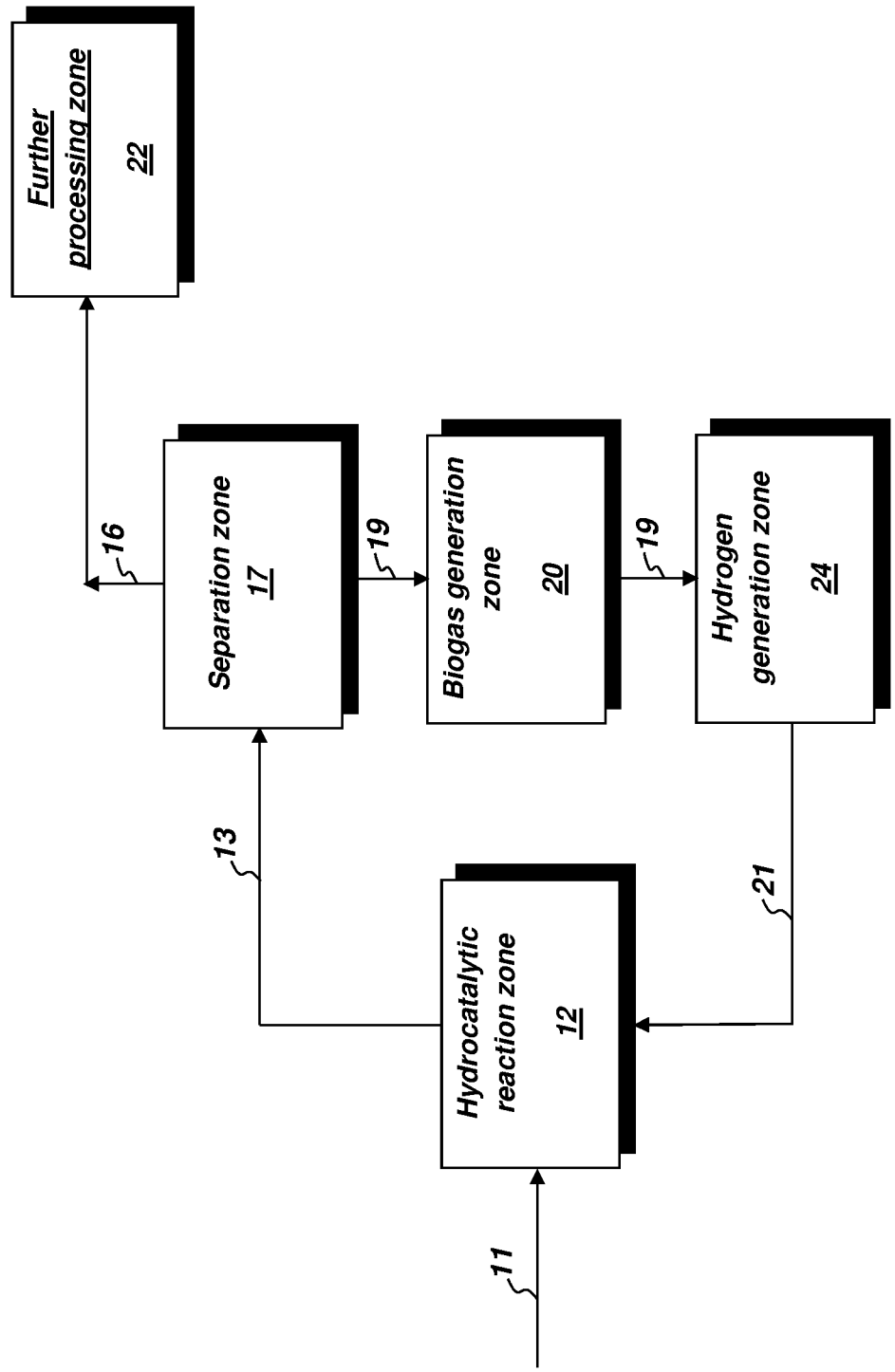

METHODS AND SYSTEMS FOR SUPPLYING HYDROGEN TO A HYDROCATALYTIC REACTION

This non-provisional application claims the benefit of U.S. Application No. 62/431,452, filed Dec. 8, 2016 the entire disclosure of which is hereby incorporated by reference.

TECHNICAL FIELD

Embodiments of the present disclosure generally relate to a hydrocatalytic reaction and more specifically, to systems and methods involving hydrocatalytic reactions that use molecular hydrogen obtained from a biogas generated from at least a portion of the hydrocatalytic reaction product.

BACKGROUND

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of any prior art.

In recent years, there have been significant concerns about greenhouse gas ("GHG") emissions and their effect on climate. GHGs, especially carbon dioxide, but also methane and nitrous oxide, trap heat in the atmosphere and thus contribute to climate change. One of the largest sources of GHG emissions is the production and use of fossil fuels for transportation, heating and electricity generation.

Significant efforts have been devoted to reducing the GHG emissions that are associated with production and use of transportation fuels. Renewable fuels, for example, are being used to displace fossil fuels in the transportation sector. Cellulosic biomass has garnered particular attention in this regard due to its abundance and the versatility of the various constituents found therein, particularly cellulose and other carbohydrates. Despite promise and intense interest, the development and implementation of bio-based fuel technology has been slow. Existing technologies have heretofore produced fuels having a low energy density (e.g., bioethanol) and/or that are not fully compatible with existing engine designs and transportation infrastructure (e.g., methanol, biodiesel, Fischer-Tropsch diesel, hydrogen, and methane). Moreover, conventional bio-based processes have typically produced intermediates in dilute aqueous solutions (>50% water by weight) that are difficult to further process. Energy- and cost-efficient processes for processing cellulosic biomass into fuel blends having similar compositions to fossil fuels would be highly desirable to address the foregoing issues and others.

The United States government, through the Energy Independence and Security Act ("EISA") of 2007, has promoted the use of renewable fuels with reduced GHG emissions. Some of the purposes of the act are to increase the production of clean renewable fuels, to promote research on and deploy GHG capture and to reduce fossil fuels present in transportation fuels. The act sets out a Renewable Fuels Standard ("RFS") with increasing annual targets for the renewable content of transportation fuel sold or introduced into commerce in the United States. The RFS mandated volumes are set by four nested fuel category groups, namely renewable biofuel, advanced biofuel, biomass-based diesel, and cellulosic biofuel, which require at least 20%, 50%, 50% and 60% GHG reductions relative to gasoline, respectively. The mandated annual targets of renewable content in transportation fuel under the RFS are implemented using a credit called a Renewable Identification Number, referred to herein as a "RIN," to track and manage the production, distribution and use of renewable fuels for transportation purposes. RINs can be likened to a currency used by obligated parties to certify compliance with mandated renewable fuel volumes. The EPA is responsible for overseeing and enforcing blending mandates and developing regulations for the generation, trading and retirement of RINs.

In addition to EISA, numerous jurisdictions, such as the state of California, the province of British Columbia, Canada and the European Union, have set annual targets for reduction in average life cycle GHG emissions of transportation fuel. Such an approach is often referred to as a Low Carbon Fuel Standard ("LCFS"), where credits may be generated for the use of fuels that have lower life cycle GHG emissions than a specific baseline fuel. Such fuels are often referred to as having a lower "carbon intensity" or "CI".

Accordingly, the efficient conversion of cellulosic biomass into fuel blends and other materials that meet certain government environmental regulations is a complex problem that presents immense engineering challenges. The present disclosure addresses these challenges and provides related advantages as well.

SUMMARY

The present disclosure describes systems and methods involving hydrocatalytic reactions that use molecular hydrogen obtained from a biogas generated from at least a portion of the hydrocatalytic reaction product.

According to one aspect, the present disclosure provides a method comprising: (a) providing cellulosic biomass solids, molecular hydrogen, a slurry catalyst capable of activating molecular hydrogen, and a digestion solvent to a hydrothermal digestion unit in a hydrocatalytic reaction zone, wherein the slurry catalyst comprises at least one of Cr, Mo, W, Re, Mn, Cu, Cd, Fe, Co, Ni, Pt, Pd, Rh, Ru, Jr, Os, and any alloys thereof; (b) heating the cellulosic biomass solids, molecular hydrogen, a catalyst capable of activating molecular hydrogen, and digestion solvent to a temperature in a range of 110 degrees to 300 degrees C. and under a pressure in a range of 30 to 450 bar to produce a reaction product comprising an alcoholic component that comprises at least one of a monohydric alcohol, a glycol, and a triol; (c) providing at least a portion of the reaction product to a separation zone to recover a top fraction comprising the alcoholic component and a bottom fraction comprising compounds having a normal boiling point of greater than 350 degrees C.; (d) providing at least a portion of the top fraction to a further processing zone to produce a higher molecular weight compound comprising >C4 hydrocarbons, wherein said further processing zone comprises a condensation reaction; (e) providing at least a portion of the bottom fraction to a biogas generation zone to produce a biogas comprising methane, wherein said biogas generation zone comprises anaerobic digestion of the bottom fraction; (f) providing at least a portion of the biogas from step (e) to a hydrogen generation zone to convert at least a portion of said biogas to molecular hydrogen; and (g) providing at least a portion of the molecular hydrogen from the hydrogen generation zone to said hydrothermal digestion unit in the hydrocatalytic reaction zone.

According to another aspect, there is provided a system comprising: (a) a hydrothermal digestion unit in a hydrocatalytic reaction zone, said hydrothermal digestion unit comprising cellulosic biomass solids, molecular hydrogen, a slurry catalyst capable of activating molecular hydrogen, and a digestion solvent to, wherein the slurry catalyst comprises at least one of Cr, Mo, W, Re, Mn, Cu, Cd, Fe, Co, Ni, Pt, Pd, Rh, Ru, Ir, Os, and any alloys thereof, wherein said hydrothermal digestion unit is configured to produce a reaction product comprising an alcoholic component that comprises at least one of a monohydric alcohol, a glycol, and a triol when the cellulosic biomass solids, molecular hydrogen, a catalyst capable of activating molecular hydrogen, and digestion solvent are heated to a temperature in a range of 110 degrees to 300 degrees C. and under a pressure in a range of 30 to 450 bar; (b) a separation zone that is in fluid communication with the hydrocatalytic zone to receive at least a portion of the reaction product, wherein the separation zone is configured to recover a top fraction comprising the alcoholic component and a bottom fraction comprising compounds having a normal boiling point of greater than 350 degrees C.; (d) a further processing zone in fluid communication with the separation zone to receive at least a portion of the top fraction, wherein the further processing zone is configured to produce a higher molecular weight compound comprising >C4 hydrocarbons, and wherein said further processing zone comprises a condensation reaction; (e) a biogas generation zone in fluid communication with the separation zone to receive at least a portion of the bottom fraction, wherein the biogas generation zone is configured to produce a biogas comprising methane, wherein said biogas generation zone comprises anaerobic digestion of the bottom fraction; and (f) a hydrogen generation zone in fluid communication with the biogas generation zone to receive at least a portion of the biogas, wherein the hydrogen generation zone is configured to convert at least a portion of said biogas to molecular hydrogen; and wherein the hydrogen generation zone is in fluid communication with the hydrocatalytic reaction zone to provide at least a portion of said molecular hydrogen to said hydrothermal digestion unit.

Other advantages and features of embodiments of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

The following FIGURE is included to illustrate certain aspects of the present disclosure, and should not be viewed as exclusive embodiments. The subject matter disclosed is capable of considerable modifications, alterations, combinations, and equivalents in form and function, as will occur to one having ordinary skill in the art and the benefit of this disclosure.

FIG. 1 shows an illustrative schematic of one embodiment to supply hydrogen to a hydrocatalytic reaction according to aspects described herein.

DETAILED DESCRIPTION

The present disclosure relates to systems and methods involving hydrocatalytic reactions that use molecular hydrogen obtained from a biogas generated from at least a portion of the hydrocatalytic reaction product. The present disclosure provides systems and methods that can allow the fuel product generated as described herein to comply with a fuel pathway specified in U.S. renewable fuel standard program (RFS) regulations or similar regulations enacted by other countries Hydrocatalytic reactions or hydrothermal reactions have been used to convert cellulosic biomass into fuel blends and other materials. In these reactions, cellulose and other complex carbohydrates therein can be extracted and transformed into simpler organic molecules, which can be further processed thereafter. Digestion is one way in which cellulose and other complex carbohydrates may be converted into a more usable form. Digestion processes can break down cellulose and other complex carbohydrates within cellulosic biomass into simpler, soluble carbohydrates that are suitable for further transformation through downstream further processing reactions. As used herein, the term "soluble carbohydrates" refers to monosaccharides or polysaccharides that become solubilized in a digestion process. Illustrative carbohydrates that may be present in cellulosic biomass solids include, for example, sugars, sugar alcohols, celluloses, lignocelluloses, hemicelluloses, and any combination thereof.

A particularly effective manner in which soluble carbohydrates may be formed is through hydrothermal digestion, in which the soluble carbohydrates may be converted into more stable compounds by subjecting them to one or more catalytic reductions, which may include hydrogenation and/or hydrogenolysis reactions. Hydrothermal digestion of a cellulosic biomass can include heating of the cellulosic biomass and a digestion solvent in the presence of molecular hydrogen and a catalyst capable of activating the molecular hydrogen (which can also be referred to herein as a "hydrogen-activating catalyst" or "hydrocatalytic catalyst"). Preferably, the catalyst is a slurry catalyst. As used herein, the term "slurry catalyst" will refer to a catalyst comprising fluidly mobile catalyst particles that can be at least partially suspended in a fluid phase via gas flow, liquid flow, mechanical agitation, or any combination thereof. In such approaches, the hydrothermal digestion of cellulosic biomass and the catalytic reduction of soluble carbohydrates produced therefrom may take place in the same vessel, which can be referred to as "in situ catalytic reduction reaction processes."

In situ catalytic reduction reaction of cellulosic biomass can be considered a hydrothermal reaction or hydrocatalytic reaction that generates a hydrothermal reaction product or a hydrocatalytic reaction product, which can contain a variety of compounds, ranging from lighter compounds in the alcoholic component to heavier compounds, including lignin and lignin-derived compounds, such as phenolics, and various compounds in between. Optionally, this reaction product, which may be referred to as a first reaction product, can be further hydrotreated in a second hydrothermal reaction in the presence of a hydrogen-activating catalyst and molecular hydrogen, which generates a second reaction product. The further hydrotreatment can convert at least a portion of the lignin and/or lignin-derived compounds, like phenolics, to hydrocarbons. Optionally, at least some of the alcoholic component in the first reaction product, such as glycol or triol, can also be converted to monohydric alcohol in the second hydrothermal reaction.

The hydrocatalytic reactions, such as in situ catalytic reduction reactions, however, can necessitate the input of significant quantities of molecular hydrogen, particularly if the molecular hydrogen is being introduced under dynamic flow conditions. The present disclosure provides systems and methods that can allow for reducing the carbon footprint of the fuels formed from the hydrocatalytic reaction because at least a portion of the hydrogen used in the hydrocatalytic reaction has low carbon footprint. A fuel with low carbon footprint can qualify for certain governmental status that provides certain benefits.

In particular, in 2005, the Environmental Protection Agency (EPA) released its Renewable Fuel Standards (RFS-I). Two years later, the program was expanded under the Energy Independence and Security Act of (EISA) of 2007, which calls for a certain amount of advanced biofuels that are non-ethanol. In 201, the EPA submitted revisions—RFS-II—to the previous renewable fuel standards (RFS-I). The RFS-I and RFS-II can be collectively referred to as RFS. Part of the regulations include an incentive program that provides for an award of Renewable Identification Numbers (RIN) for the production of fuels in accordance with certain pathways that are designed to be environmentally less harmful than the traditional methods of producing fuels. Among the several approved pathways, there are some related to the use of cellulosic containing biomass (cellulosic biomass) that can earn Cellulosic Renewable Identification Numbers (C-RIN's). The use of cellulosic biomass can also aid fuel producers in meeting their Renewable Volume Obligations (RVO) as well.

The present disclosure provides, in certain embodiments, a fuel product (for example diesel fuel and/or gasoline) that complies with U.S. renewable fuel standard program (RFS) regulations for generating the cellulosic renewable identification number. In certain embodiments, the fuel product may be produced via a fuel pathway specified in U.S. RFS regulations for generating cellulosic renewable identification numbers. For example, the pathway may include a cellulosic fuel pathway, a cellulosic renewable identification number-compliant pathway, a pathway compliant in generating, producing, preparing, or making, a cellulosic renewable identification number-compliant fuel, or a pathway that complies with a fuel pathway specified in U.S. RFS regulations for generating the cellulosic renewable identification number. The present disclosure provides embodiments that also allow fuel producers to qualify for desired credits associated with reduced GHG life cycle emissions, including for example RINs under EISA associated with lower GHG emissions.

For example, to achieve cellulosic biofuel status, a 60% reduction from standard reference petroleum gasoline value of 91.6 grams $CO_2$ emitted/Megajoule of fuel ($gCO_2e/MJ$). The target GHG emissions for cellulosic biofuels under RFS-II is about 36.6 $gCO_2e/MJ$. Similarly, the target for advanced biofuels would be about 45.8 $gCO_2e/MJ$. Reduction in the overall production process GHG emissions of the fuel produced is desired. One way for such reduction is to reduce the amount of fossil fuels, such as natural gas, used in the process. In one exemplary process, approximately every 43 kiloton per year of natural gas combusted contributes approximately 10 $gCO_2e/MJ$ of the fuel generated in such process. As such, reducing the amount of natural gas that needs to be combusted (e.g., to provide hydrogen) to produce a fuel reduces the amount of $CO_2$ that is added to the emissions in calculating which category the fuel would qualify in a certain government program, such as RFS-II Eliminating $CO_2$ emissions by combusting less natural gas facilitates achievement of the highest valued category of fuel in a government program, such as biofuel, particularly cellulosic biofuel, in the RFS-II, which typically requires the lowest amount of $CO_2$ emitted per MJ of fuel. Natural gas used as a source of hydrogen through steam methane reforming also leads to higher GHG emissions. As such, using a portion of the hydrocatalytic reaction product to generate a biogas which is then converted to molecular hydrogen instead of using natural gas as a source of hydrogen can eliminate additional carbon dioxide from being added to the emissions for the fuel being produced, which allows the fuel to potentially more readily meet the requirements for a more favorable fuel status under a particular government program. That is, at least part of the hydrogen used by the process comes from a renewable source, which is the reaction product of the cellulosic biomass solids.

As used herein, the term "biogas" refers to a combustible fluid feedstock comprising methane that has been converted from a material comprising organic matter, where the biogas may be produced by anaerobic digestion of organic material.

The term "hydrocatalytic reaction" or "hydrothermal reaction" refers to a type of thermocatalytic reaction where the reaction is with hydrogen in the presence of a catalyst capable of activating molecular hydrogen, preferably a metal catalyst.

The term "alcoholic component" refers to an oxygenate where the oxygenate can be a monohydric alcohol, a glycol, a triol, or any combination thereof. As used herein, the term "glycol" will refer to compounds containing two alcohol functional groups, two alcohol functional groups and a carbonyl functionality, or any combination thereof. As used herein, the term "carbonyl functionality" will refer to an aldehyde functionality or a ketone functionality. In some embodiments, a glycol may comprise a significant fraction of the reaction product. Although a glycol may comprise a significant fraction of the reaction product, it is to be recognized that other alcohols, including triols and monohydric alcohols, for example, may also be present. Further, any of these alcohols may further include a carbonyl functionality. As used herein, the term "triol" will refer to compounds containing three alcohol functional groups, three alcohol functional groups and a carbonyl functionality, and any combination thereof. As used herein, the term "monohydric alcohol" will refer to compounds containing one alcohol functional group, one alcohol functional group and a carbonyl functionality, and any combination thereof. Monohydric alcohol can include compounds that may be characterized as mono-oxygenated hydrocarbon compounds.

The term "phenolics" or "phenols" has its ordinary meaning, which generally refers to a class of compounds that contain a hydroxyl group (—OH) bonded to an aromatic hydrocarbon group. The terms "hydrocarbon compounds," "hydrocarbons," or related terms refer to compounds comprising hydrogen and carbon atoms and do not contain a phenolic functional group, which is a hydroxyl group (—OH) bonded to an aromatic hydrocarbon group. Illustrative, non-limiting hydrocarbon compounds include alkanes, alkenes, cycloalkanes and their alkyl substituents or derivatives, and cycloalkenes and their alkyl substituents or derivatives, which can be suitable for use in fuel composition, for instance gasoline or diesel. For instance, illustrative hydrocarbon compounds can include but are not limited to cyclohexane, cyclohexene, propyl cyclopentane, propyl cyclopentene, propyl cyclohexane, propyl cyclohexene, anisole, propyl benzene, cyclohexanone, methyl cyclohexanone, and methyl propyl benzene.

The term "credit" or "renewable fuel credit" means any rights, credits, revenues, offsets, greenhouse gas rights or similar rights related to carbon credits, rights to any greenhouse gas emission reductions, carbon-related credits or equivalent arising from emission reduction trading or any quantifiable benefits (including recognition, award or allocation of credits, allowances, permits or other tangible rights), whether created from or through a governmental authority, a private contract or otherwise. According to one embodiment of the invention, the renewable fuel credit is a certificate, record, serial number or guarantee, in any form, including electronic, which evidences production of a quantity of fuel meeting certain life cycle GHG emission reductions relative to a baseline set by a government authority. Preferably, the baseline is a gasoline baseline. Non-limiting examples of credits include RINs and LCFS credits.

The present disclosure provides further details with reference to the drawings. When like elements are used in one or more figures, identical reference characters will be used in each FIGURE, and a detailed description of the element will be provided only at its first occurrence. Some features of the embodiments may be omitted in certain depicted configurations in the interest of clarity. Moreover, certain features such as, but not limited to, pumps, valves, gas bleeds, gas inlets, fluid inlets, fluid outlets and the like have not necessarily been depicted in the figures, but their presence and function will be understood by one having ordinary skill in the art.

Referring to FIG. 1, biomass feedstock is provided to hydrocatalytic reaction zone 12 via line 11 where the biomass feedstock is reacted with hydrogen in the presence of a catalyst capable of activating molecular hydrogen to produce a hydrocatalytic reaction product. As shown, the hydrocatalytic reaction product is provided to separation zone 17 via line 13 to recover at least a top fraction and a bottom fraction. At least a portion of the top fraction is provided to further processing zone 22 via line 16 to produce a product stream comprising higher molecular weight compounds, which may be recovered via line 23. The bottom fraction is provided to biogas generation zone 19 via line 18.

In biogas generation zone 20, bottom fraction 19 comprising organic material is converted to a combustible fluid feedstock comprising methane, or biogas, which is provided to hydrogen generation zone 24 via stream 19. In hydrogen generation zone 24, at least a portion of the biogas is converted to molecular hydrogen, at least a portion of which is provided to hydrocatalytic reaction zone via hydrogen containing stream 21. It is understood that the hydrogen needs of hydrocatalytic reaction hydrocatalytic reaction zone 12 may be met at least by hydrogen generation zone 24 via stream 21 or additional hydrogen can also be provided to hydrocatalytic reaction zone 12 as needed, for example, during start up when hydrogen generation zone 24 may not yet generate a sufficient amount of hydrogen.

Any suitable type of biomass can be used as the biomass feedstock. Suitable cellulosic biomass sources may include, for example, forestry residues, agricultural residues, herbaceous material, municipal solid wastes, waste and recycled paper, pulp and paper mill residues, and any combination thereof. Thus, in some embodiments, a suitable cellulosic biomass may include, for example, corn stover, straw, bagasse, miscanthus, sorghum residue, switch grass, bamboo, water hyacinth, duckweed, hardwood, hardwood chips, hardwood pulp, softwood, softwood chips, softwood pulp, and any combination thereof. Leaves, roots, seeds, stalks, husks, and the like may be used as a source of the cellulosic biomass. Common sources of cellulosic biomass may include, for example, agricultural wastes (e.g., corn stalks, straw, seed hulls, sugarcane leavings, nut shells, and the like), wood materials (e.g., wood or bark, sawdust, timber slash, mill scrap, and the like), municipal waste (e.g., waste paper, yard clippings or debris, and the like), and energy crops (e.g., poplars, willows, switch grass, alfalfa, prairie bluestream, corn, soybeans, and the like). The cellulosic biomass may be chosen based upon considerations such as, for example, cellulose and/or hemicellulose content, lignin content, growing time/season, growing location/transportation cost, growing costs, harvesting costs, and the like.

The biomass feedstock may be natively present in any sizes, shapes, or forms, or it may be further processed prior to entering hydrocatalytic reaction hydrocatalytic reaction zone 12. Examples of further processing include washing (such as, with water, an acid, a base, combinations thereof, and the like), torrefaction, liquefaction, such as pyrolysis, or reduction in size. In some embodiments, the reduction in size may include chopping, grounding, shredding, pulverizing, and the like to produce a desired size. Thus, in some embodiments, providing a biomass material can comprise harvesting a lignocelluloses-containing plant such as, for example, a hardwood or softwood tree. The tree can be subjected to debarking, chopping to wood chips of desirable thickness, and washing to remove any residual soil, dirt and the like.

The biomass feedstock is preferably treated to convert the cellulose and other complex carbohydrates into a more usable form, which can be further transformed into compounds with one or more alcohol functional groups through downstream reactions. While suitable for further transformation, soluble carbohydrates can be very reactive and can rapidly degrade to produce caramelans and other degradation products, especially under higher temperature conditions, such as above about 150° C. One way to protect soluble carbohydrates from thermal degradation is to subject them to one or more catalytic reduction reactions, which may include hydrogenation and/or hydrogenolysis reactions. Depending on the reaction conditions and catalyst used, reaction products formed as a result of conducting one or more catalytic reduction reactions on soluble carbohydrates may comprise, as mentioned, one or more alcohol functional groups, particularly including triols, diols, monohydric alcohols, and any combination thereof, some of which may also include a residual carbonyl functionality (e.g., an aldehyde or a ketone). Such reaction products are typically more thermally stable than soluble carbohydrates and may be readily transformable into fuel blends and other materials through conducting one or more downstream further processing reactions. That is, soluble carbohydrates formed during hydrothermal digestion may be intercepted and converted into more stable compounds before they have an opportunity to significantly degrade, even under thermal conditions that otherwise promote their degradation.

Hydrocatalytic Reaction Zone

Any suitable hydrocatalytic reaction can take place in hydrocatalytic reaction zone 12 where at least a portion of the biomass feedstock is contacted with a catalyst that is capable of activating molecular hydrogen in the presence of molecular hydrogen. Exemplary hydrocatalytic reactions or hydrothermal reactions include hydrogenation and/or hydrogenolysis reactions. Descriptions of exemplary suitable hydrocatalytic reactions that can take place in hydrocatalytic reaction zone 12 are known to those skilled in the art Accordingly, the details of hydrocatalytic reactions need not be repeated. Nevertheless, the descriptions below highlight some aspects of certain hydrocatalytic reactions, such as in situ catalytic reduction where hydrothermal digestion and catalytic reduction reactions take place in the same vessel. It is understood that hydrocatalytic reaction zone 12 can comprise any number, combination, and type of reactors to perform one or more hydrocatalytic reactions.

Hydrocatalytic reaction zone 12 comprises a hydrothermal digestion unit in a biomass conversion system where hydrothermal digestion and one or more catalytic reduction reactions take place in that hydrothermal digestion unit, which can provide an effective stabilization of soluble carbohydrates via in situ catalytic reduction. As noted above, the foregoing may be accomplished by including a slurry catalyst capable of activating molecular hydrogen within a hydrothermal digestion unit containing cellulosic biomass solids. That is, the catalyst that is capable of activating molecular hydrogen may comprise a slurry catalyst. Formation of the reaction product may reduce the amount of thermal decomposition that occurs during hydrothermal digestion, thereby enabling high yield conversion of cellulosic biomass solids into a desired reaction product to take place in a timely manner.

Continuous, high temperature hydrothermal digestion may be accomplished by configuring the biomass conversion system in hydrocatalytic reaction zone 12 such that fresh biomass may be continuously or semi-continuously supplied to the hydrothermal digestion unit, while it operates in a pressurized state. As used herein, the term "continuous addition" and grammatical equivalents thereof will refer to a process in which cellulosic biomass is added to a hydrothermal digestion unit in an uninterrupted manner without fully depressurizing the hydrothermal digestion unit. As used herein, the term "semi-continuous addition" and grammatical equivalents thereof will refer to a discontinuous, but as-needed, addition of biomass to a hydrothermal digestion unit without fully depressurizing the hydrothermal digestion unit.

Since a slurry catalyst can be fluidly mobile, hydrogen sparge, solvent recycle, or any combination thereof may be used to distribute the slurry catalyst throughout the cellulosic biomass charge in the hydrothermal digestion unit. Good catalyst distribution in the cellulosic biomass may improve yields by intercepting soluble carbohydrates before they have an opportunity to degrade. Furthermore, use of a slurry catalyst may allow a fixed bed digestion unit to be more successfully used, since mechanical stirring or like mechanical agitation is not needed to affect catalyst distribution. This can allow higher biomass to solvent ratios to be utilized per unit volume of the digestion unit than would be possible in stirred tank or like digestion unit configurations. Furthermore, since stirring is not necessary, there is no express need to alter the size of the biomass solids prior to digestion taking place.

Catalysts capable of activating molecular hydrogen and conducting a catalytic reduction reaction may comprise a metal such as, for example, Cr, Mo, W, Re, Mn, Cu, Cd, Fe, Co, Ni, Pt, Pd, Rh, Ru, Ir, Os, and alloys or any combination thereof, either alone or with promoters such as Au, Ag, Cr, Zn, Mn, Sn, Bi, B, O, and alloys or any combination thereof. In some embodiments, the catalysts and promoters may allow for hydrogenation and hydrogenolysis reactions to occur at the same time or in succession of one another. In some embodiments, such catalysts may also comprise a carbonaceous pyropolymer catalyst containing transition metals (e.g., Cr, Mo, W, Re, Mn, Cu, and Cd) or Group VIII metals (e.g., Fe, Co, Ni, Pt, Pd, Rh, Ru, Ir, and Os). In some embodiments, the foregoing catalysts may be combined with an alkaline earth metal oxide or adhered to a catalytically active support. In some or other embodiments, the catalyst capable of activating molecular hydrogen may be deposited on a catalyst support that is not itself catalytically active.

Optionally, the hydrogen-activating catalyst may comprise a poison-tolerant catalyst. As used herein the term "poison-tolerant catalyst" refers to a catalyst that is capable of activating molecular hydrogen without needing to be regenerated or replaced due to low catalytic activity for at least about 12 hours of continuous operation. Use of a poison-tolerant catalyst may be particularly desirable when reacting soluble carbohydrates derived from cellulosic biomass solids that have not had catalyst poisons removed therefrom.

Suitable poison-tolerant catalysts may include, for example, sulfided catalysts. In some or other embodiments, nitrided catalysts may be used as poison-tolerant catalysts. Sulfided catalysts suitable for activating molecular hydrogen are described in commonly owned U.S. patent application Ser. No. 13/495,785, and 61/553,591, each of which is incorporated herein by reference in its entirety. Slurry catalysts suitable for use in the methods described herein may be sulfided by dispersing a slurry catalyst in a fluid phase and adding a sulfiding agent thereto. Suitable sulfiding agents may include, for example, organic sulfoxides (e.g., dimethyl sulfoxide), hydrogen sulfide, salts of hydrogen sulfide (e.g., NaSH), and the like.

Catalysts that are not particularly poison-tolerant may also be used in conjunction with the techniques described herein. Such catalysts may include, for example, Ru, Pt, Pd, or compounds thereof disposed on a solid support such as, for example, Ru on titanium dioxide or Ru on carbon. Although such catalysts may not have particular poison tolerance, they may be regenerable, such as through exposure of the catalyst to water at elevated temperatures, which may be in either a subcritical state or a supercritical state.

Optionally, the slurry catalyst may be operable to generate molecular hydrogen. For example, in some embodiments, catalysts suitable for aqueous phase reforming (i.e., APR catalysts) may be used. Suitable APR catalysts may include, for example, catalysts comprising platinum, palladium, ruthenium, nickel, cobalt, or other Group VIII metals alloyed or modified with rhenium, molybdenum, tin, or other metals, or sulfided. However, in other embodiments, an external hydrogen feed may be used, optionally in combination with internally generated hydrogen.

Slurry catalysts used in embodiments described herein may have a particulate size of about 250 microns or less. Optionally, the slurry catalyst may have a particulate size of about 100 microns or less, or about 10 microns or less. The minimum particulate size of the slurry catalyst may be about 1 micron.

In general, digestion in the hydrothermal digestion unit may be conducted in a liquor phase comprising a digestion solvent that may comprise water. Optionally, the liquor phase may further comprise an organic solvent. Although any organic solvent that is at least partially miscible with water may be used as a digestion solvent, particularly advantageous organic solvents are those that can be directly converted into fuel blends and other materials without being separated from the hydrocatalytic reaction product. That is, particularly advantageous organic solvents are those that may be co-processed along with the hydrocatalytic reaction product into fuel blends and other materials during further processing reactions. Suitable organic solvents in this regard may include, for example, ethanol, ethylene glycol, propylene glycol, glycerol, phenolics, and any combination thereof. In some embodiments, the organic solvent may comprise oxygenated intermediates produced from a catalytic reduction reaction of soluble carbohydrates. For example, in some embodiments, a digestion solvent may comprise oxygenated intermediates produced by a hydrogenolysis reaction or other catalytic reduction reaction of soluble carbohydrates. In some embodiments, the oxygenated intermediates may include those produced from an in situ catalytic reduction reaction and/or from the catalytic reduction reactor unit.

In some embodiments employing hydrothermal digestion, the digestion solvent may further comprise a small amount of a monohydric alcohol. The presence of at least some monohydric alcohols in the fluid phase digestion medium may desirably enhance the hydrothermal digestion and/or the catalytic reduction reactions being conducted therein. For example, inclusion of about 1% to about 5% by weight monohydric alcohols in the fluid phase digestion medium may desirably maintain catalyst activity due to a surface cleaning effect. Monohydric alcohols present in the digestion solvent may arise from any source. In some embodiments, the monohydric alcohols may be formed via the in situ catalytic reduction reaction process being conducted therein. In some or other embodiments, the monohydric alcohols may be formed during further chemical transformations of the initially formed the hydrocatalytic reaction product. In still other embodiments, the monohydric alcohols may be sourced from an external feed that is in flow communication with the cellulosic biomass solids.

In some embodiments, the digestion solvent may comprise between about 1% water and about 99% water. Although higher percentages of water may be more favorable from an environmental standpoint, higher quantities of organic solvent may more effectively promote hydrothermal digestion due to the organic solvent's greater propensity to solubilize carbohydrates and promote catalytic reduction of the soluble carbohydrates. In some embodiments, the digestion solvent may comprise about 90% or less water by weight. In other embodiments, the digestion solvent may comprise about 80% or less water by weight, or about 70% or less water by weight, or about 60% or less water by weight, or about 50% or less water by weight, or about 40% or less water by weight, or about 30% or less water by weight, or about 20% or less water by weight, or about 10% or less water by weight, or about 5% or less water by weight.

In some embodiments, the digestion solvent may comprise an organic solvent comprising oxygenated intermediates resulting from a catalytic reduction reaction of soluble carbohydrates. In some embodiments, the organic solvent may comprise at least one alcohol, ketone, or polyol. In alternative embodiments, the digestion solvent may be at least partially supplied from an external source. For example, in some embodiments, bio-ethanol may be used to supplement the organic solvent. Other water-miscible organic solvents may be used as well. In some embodiments, the digestion solvent may be separated, stored, or selectively injected into the hydrothermal digestion unit so as to maintain a desired concentration of soluble carbohydrates or to provide temperature regulation in the hydrothermal digestion unit.

In situ catalytic reduction reactions may take place in the hydrothermal digestion unit of hydrocatalytic reaction zone 12 over a period of time at elevated temperatures and pressures. The content of the hydrothermal digestion unit comprising cellulosic biomass solids, a digestion solvent, a catalyst capable of activating hydrogen, and hydrogen is heated to form a hydrocatalytic reaction product comprising phenols and an alcoholic component. The content of the hydrothermal digestion unit can be heated to a temperature in a range of 110 degrees to 300 degrees C., including about 160 to 280 degrees C., such as in a range of about 180 to 270 degrees C., including in a range of about 190 to 260 degrees C. For instance, the content of the hydrothermal digestion unit can be heated to at least 180 degrees C., at least 190 degrees C., at least 200 degrees C., at least 210 degrees C., at least 220 degrees C., at least 230 degrees C., at least 240 degrees C., at least 250 degrees C., at least 260 degrees C., at least 270, at least 280, at least 290, or at least 300 degrees C. The content of the hydrothermal digestion unit can be heated to at most 300 degrees C., at most 275 degrees C., at most 250 degrees C., at most 225 degrees C., at most 200 degrees C., at most 175 degrees C., or at most 150 degrees C.

The heating of the content of the hydrothermal digestion unit is preferably performed under a pressurized state. As used herein, the term "pressurized state" refers to a pressure that is greater than atmospheric pressure (1 bar). For example, the hydrothermal digestion unit may have a pressure of at least about 30 bar, such as at least about 45 bar, at least about 60 bar, at least about 75 bar, at least about 90 bar, at least about 100 bar, at least about 110 bar, at least about 120 bar, or at least about 130. The hydrothermal digestion unit may have a pressure of at most about 450 bar, such as at most about 330 bar, at most about 200 bar, at most about 175 bar, at most about 150 bar, or at most about 130 bar. As such, the hydrothermal digestion unit may have a pressure in a range of about 30 to 450 bar.

The content of the hydrothermal digestion unit may be heated for at least 30 minutes and up to 10 hours. For example, it may be heated for at least 30 minutes, at least 60 minutes, at least 120 minutes, at least 180 minutes, at least 240 minutes, at least 300 minutes, at least 360 minutes, at least 420 minutes, at least 480 minutes, at least 540 minutes, or at least 600 minutes. Heating of the content of the hydrothermal digestion unit may be carried out at most 600 minutes, at most 540 minutes, at most 480 minutes, at most 420 minutes, at most 360 minutes, at most 300 minutes, at most 240 minutes, at most 180 minutes, at most 120 minutes, at most 60 minutes, or at most 30 minutes.

Separation Zone

Referring to FIG. 1, at least a portion of the hydrocatalytic reaction product is provided to separation zone 17, which can separate the reaction product into at least a top fraction comprising the alcoholic component and a the bottom fraction comprising compounds having a normal boiling point of greater than 350 degrees C. The top fraction can be provided to further processing zone 22 via line 16. The bottom fraction can be provided to coking zone 19 via line 18. Separation zone 17 can comprise one or more mechanisms that separate the compounds in the hydrocatalytic reaction product based on certain properties, such as boiling point and miscibility. It is common general knowledge that distillation is an illustrative manner to separate compounds based on boiling points. For instance, separation zone 17 can comprise a liquid-liquid separation mechanism step that generates an aqueous phase and a non-aqueous phase, where the aqueous phase has more water than the non-aqueous phase. Non-limiting examples of liquid-liquid separation mechanisms include liquid-liquid extraction or phase separation. The non-aqueous phase can then be subject to distillation, flashing, or other separation techniques to generate a bottom fraction comprising compounds having a normal boiling point of greater than 350 degrees C. Further illustrative embodiments of the separation zone are provided in U.S. Publication Nos. US20160184795; US20160184796; US20160186068; US20160184797; US20160184734; US20160186073; and US20160186067; the disclosures of which are incorporated by reference in their entirety.

Further Processing Zone

As shown, the top fraction provided via line 16 may be further processed into a biofuel in further processing zone 22, which may generally comprise a condensation reaction, often conducted in the presence of a condensation catalyst, in which the alcoholic component or a product formed therefrom is condensed with another molecule to form a higher molecular weight compound. The product generated in further processing zone 22 may be recovered via line 23. As used herein, the term "condensation reaction" will refer to a chemical transformation in which two or more molecules are coupled with one another to form a carbon-carbon bond in a higher molecular weight compound, usually accompanied by the loss of a small molecule such as water or an alcohol. An illustrative condensation reaction is the Aldol condensation reaction, which will be familiar to one having ordinary skill in the art.

Although a number of different types of catalysts may be used for mediating condensation reactions, zeolite catalysts also may be particularly advantageous in this regard. One zeolite catalyst that may be particularly well suited for mediating condensation reactions of alcohols is ZSM-5 (Zeolite Socony Mobil 5), a pentasil aluminosilicate zeolite having a composition of $Na_nAl_nSi_{96-n}O_{192} \cdot 6H_2O$ (0<n<27), which may transform an alcohol feed into a condensation product. Other suitable zeolite catalysts may include, for example, ZSM-12, ZSM-22, ZSM-23, SAPO-11, and SAPO-41.

The condensation reaction may take place at a temperature ranging between about 275 degrees C. and about 450 degrees C. The condensation reaction may take place in a condensed phase (e.g., a liquor phase) or in a vapor phase. For condensation reactions taking place in a vapor phase, the temperature may range between about 300 degrees C. and about 400 degrees C., such as 350 degrees C. or above. The condensation reaction may take place at a pressure in a range of about 5 bar to 50 bar, such as 10 bar to 30 bar, including about 15 bar to 20 bar.

Reactions in further processing zone 22, such as a condensation reaction, produce a higher molecular weight compound, which may comprise >C4 hydrocarbons, such as C4-C30 hydrocarbons, C4-C24 hydrocarbons, C4-C18 hydrocarbons, or C4-C12 hydrocarbons; or >C6 hydrocarbons, such as C6-C30 hydrocarbons, C6-C24 hydrocarbons, C6-C18 hydrocarbons, or C6-C12 hydrocarbons. Consistent with the description provided above, the term "hydrocarbons" refers to compounds containing both carbon and hydrogen without reference to other elements that may be present other than exclusion of a phenolics group as described above. Thus, certain heteroatom-substituted compounds are also described herein by the term "hydrocarbons." The particular composition of the higher molecular weight compound produced by the condensation reaction may vary depending on the catalyst(s) and temperatures used for both the catalytic reduction reaction and the condensation reaction, as well as other parameters such as pressure.

A single catalyst may mediate the transformation of the alcoholic component into a form suitable for undergoing a condensation reaction as well as mediating the condensation reaction itself. Zeolite catalysts are one type of catalyst suitable for directly converting alcohols to condensation products in such a manner. A particularly suitable zeolite catalyst in this regard may be ZSM-5, although other zeolite catalysts may also be suitable.

On the other hand, a first catalyst may be used to mediate the transformation of the alcoholic component into a form suitable for undergoing a condensation reaction, and a second catalyst may be used to mediate the condensation reaction. Unless otherwise specified, it is to be understood that reference herein to a condensation reaction and condensation catalyst refers to either type of condensation process. Further disclosure of suitable condensation catalysts now follows. Zeolite catalysts may be used as either the first catalyst or the second catalyst. Again, a particularly suitable zeolite catalyst in this regard may be ZSM-5, although other zeolite catalysts may also be suitable.

Various catalytic processes may be used to form higher molecular weight compounds by a condensation reaction. In some embodiments, the catalyst used for mediating a condensation reaction may comprise a basic site, or both an acidic site and a basic site. Catalysts comprising both an acidic site and a basic site will be referred to herein as multi-functional catalysts. In some or other embodiments, a catalyst used for mediating a condensation reaction may comprise one or more metal atoms. Any of the condensation catalysts may also optionally be disposed on a solid support, if desired. Additional details regarding suitable catalysts are described in commonly owned U.S. patent application Ser. No. 14/067330, filed Oct. 30, 2013, and entitled Methods and Systems for Processing Lignin During Hydrothermal Digestion of Cellulosic Biomass Solids," the entire disclosure of which is incorporated herein by reference.

For example, the condensation catalyst may also include a zeolite and other microporous supports that contain Group IA compounds, such as Li, Na, K, Cs and Rb. Preferably, the Group IA material may be present in an amount less than that required to neutralize the acidic nature of the support. A metal function may also be provided by the addition of group VIIIB metals, or Cu, Ga, In, Zn or Sn. In some embodiments, the condensation catalyst may be derived from the combination of MgO and $Al_2O_3$ to form a hydrotalcite material. Another condensation catalyst may comprise a combination of MgO and ZrO2, or a combination of ZnO and $Al_2O_3$. Each of these materials may also contain an additional metal function provided by copper or a Group VIIIB metal, such as Ni, Pd, Pt, or combinations of the foregoing.

The condensation reaction mediated by the condensation catalyst may be carried out in any reactor of suitable design, including continuous-flow, batch, semi-batch or multi-system reactors, without limitation as to design, size, geometry, flow rates, and the like. The reactor system may also use a fluidized catalytic bed system, a swing bed system, fixed bed system, a moving bed system, or a combination of the above. In some embodiments, bi-phasic (e.g., liquid-liquid) and tri-phasic (e.g., liquid-liquid-solid) reactors may be used to carry out the condensation reaction.

Biogas Generation Zone

Referring to FIG. 1, at least a portion of bottom fraction 18 is provided to biogas generation zone 19. In biogas generation zone 19, bottom fraction 18 comprising organic material is subjected to anaerobic digestion to generate biogas. "Anaerobic digestion" is the biological breakdown of organic material by microorganisms under low oxygen conditions, or in the absence of oxygen, to produce a gas comprising methane, referred to herein as biogas. As used herein, the term encompasses any method for microbially digesting organic matter under anaerobic conditions. The anaerobic digestion may or may not be contained within an anaerobic digester, as described further below.

Biogas generation zone 18 may comprise a biogas production facility that produces biogas either as a target product or as a co-product and includes an agricultural, municipal or industrial operation. This includes, without limitation, a landfill, a facility containing anaerobic digesters, a waste treatment facility, such as a sewage treatment facility, and a manure digestion facility, such as a facility located on a farm or processing materials collected from farms. That is, the feed for a biogas production facility of biogas generation zone 19 comprises bottom fraction 18, and optionally organic material from other sources, such as waste organic material, including animal waste material and animal byproducts; separated yard waste or food waste, including recycled cooking and trap grease; and landfill waste, including, but not limited to, food and yard waste.

As noted above, anaerobic digestion may be carried out in an anaerobic digester. An anaerobic digester is a tank, or other contained volume, such as a covered lagoon, designed to facilitate the breakdown of organic material or biomass by microorganisms under anaerobic or low oxygen conditions. The anaerobic digestion may be carried out in one or multiple anaerobic digesters. An anaerobic digester utilized in accordance with the invention may be designed and/or operated in a number of configurations including batch or continuous, mesophilic or thermophilic temperature ranges, and low, medium or high rates. The rate refers to the chemical oxygen demand (COD) feed rate to the unit, which is a rate measurement based on the organic compounds present in the feed. In practice, the choice of configuration will depend on a number of factors. These may include consideration of the nature of the organic material or biomass to be treated and/or the level of treatment desired. Other factors that may be considered in the configuration choice include operating parameters such as residence time, temperature, pH and the nutrients supplied to a digester.

Anaerobic digestion generates crude biogas that can be collected by suitable mechanisms known to one of ordinary skill, such as those disclosed in U.S. Pat. Nos. 7,951,296 and 7,972,082 and WO 2010/051622, each of which is incorporated herein by reference. Apart from the methane, the crude biogas typically contains one or more impurities such as carbon dioxide, hydrogen sulfide, water, oxygen, nitrogen and halogenated compounds. The impurities in the crude biogas can be removed by any suitable method, or combination of methods to yield relatively purified combustible fluid feedstock. The crude biogas can be purified to any degree, including, but not limited to, the extent required to meet pipeline specifications. Although typically in gas form, the combustible fluid feedstock can be a liquid or a gas. In a preferred embodiment of the invention, at least carbon dioxide is removed from the crude biogas, although other impurities can optionally be removed as well.

Carbon dioxide removal from the crude biogas may be carried out by scrubbing techniques such as water or polyethylene glycol scrubbing, which involve flowing biogas through a column with a water or polyethylene glycol solution flowing counter-current to the biogas. Carbon dioxide is removed from the crude biogas by these techniques since it is more soluble in water or polyethylene glycol than methane.

A further technique for carbon dioxide removal from the crude biogas is pressure swing absorption, which utilizes adsorptive materials, such as zeolites and activated carbon that preferentially adsorb carbon dioxide at high pressure. When the pressure is released, the carbon dioxide desorbs.

Membrane separation is another technique that can be used to remove carbon dioxide from the crude biogas. Membrane separation may include high pressure gas separation or gas-liquid absorption membranes.

Removal of hydrogen sulfide from the crude biogas may be carried out by bacteria, such as chemotrophic thiobacteria that are capable of oxidizing hydrogen sulfide and using carbon dioxide as a carbon source. Bacterial removal of hydrogen sulfide may be carried out in an anaerobic digester or a storage tank. The addition of oxygen into a digester or storage tank promotes the growth of indigenous thiobacteria. Optionally, removal of hydrogen sulfide by bacteria may be combined with water scrubbing. Another illustrative method for removing hydrogen sulfide is the addition of iron chloride to an anaerobic digester. The iron chloride reacts with hydrogen sulfide that is produced to form iron sulfide salt. Other non-limiting examples of techniques that can be utilized to remove hydrogen sulfide include the addition of iron oxide to a digester, which reacts with hydrogen sulfide to produce iron sulfide, pressure swing absorption, water scrubbing, polyethylene glycol scrubbing and sodium hydroxide scrubbing.

Halogenated hydrocarbons can be removed by contacting the biogas with activated carbon. Oxygen and nitrogen impurities can be removed by membranes or pressure swing adsorption.

Hydrogen Generation Zone

Referring to FIG. 1, at least a portion of crude biogas, optionally purified, can be provided to hydrogen generation zone 24 via biogas containing stream 20. In hydrogen generation zone 24, production of hydrogen from the biogas may be carried out by any suitable means known to those of skill in the art. For instance, non-limiting examples of such suitable mechanisms include autothermal reforming ("ATR") and steam methane reforming ("SMR"). Both ATR and SMR methods operate by exposing the biogas or methane therein to a catalyst at high temperature and pressure to produce syngas, which contains hydrogen and carbon monoxide. The carbon monoxide generated by either method may be generally further reacted with water in a water gas shift reaction to form carbon dioxide and hydrogen. SMR converts the methane into hydrogen and carbon monoxide without oxygen. Without being limiting, conventional steam reforming plants may operate at pressures between 200 and 600 psi with outlet temperatures in the range of 815 to 925° C.

ATR uses oxygen and carbon dioxide or steam in a reaction with methane to form syngas and water. A difference between SMR and ATR is that SMR uses no oxygen. SMR and ATR are carried out in any suitable device or devices for producing renewable hydrogen from a combustible fluid feedstock and include devices and operations that are known or used in the art for such purposes. The steam reforming operation may be situated in the fuel production facility or the operation may be a separate plant located off-site. Molecular hydrogen generated in hydrogen generation zone 24 may then be provided to hydrocatalytic zone via hydrogen stream 21 for use in one or more hydrocatalytic reactions.

Meeting Renewable and Low Carbon Fuel Targets

The higher molecular weight compounds produced as described herein may qualify for the generation of RINs under the EISA legislation, and LCFS credits under AB 32 as a result of the renewable nature and favorable GHG profile of the input biogas. A RIN is a certificate which acts as a tradable currency for managing compliance under the RFS, and an LCFS credit is a certificate which acts as a tradable currency for managing compliance under California's LCFS. A RIN has numerical information associated with the production of a qualifying renewable fuel in accordance with regulations administered by the EPA for the purpose of managing the production, distribution and use of renewable fuels for transportation or other purposes. As described previously, the utilization of renewable feedstocks to produce transportation or heating fuel has been promoted by various governments, including the United States government through the EISA legislation. One of the goals of the act is to increase the production and use of clean renewable fuels. In order to achieve this objective, EISA mandates the use of aggregate volumes of different categories of renewable biofuels within the total pool of transportation or heating fuels sold or introduced into commerce in the United States.

The mandated annual targets of renewable content in transportation or heating fuel are implemented through an RFS program that uses RINs to track and manage the production, distribution and use of renewable fuels for transportation or heating purposes. Prorated mandated volume requirements are determined for each "obligated party", such as individual gasoline and diesel producers and/or importers, based on their annual production and/or imports. Each year, obligated parties are required to meet their prorated share of the RFS mandates by accumulating trading certificates, such as RINs, either through blending designated quantities of different categories of biofuels, or by purchasing from others the RINs of the required biofuel categories. In the U.S., the EPA is responsible for developing regulations for RINs, as required by section 211(o) of the Clean Air Act, as amended by EISA.

The EPA issued regulations in 2007 referred to as "RFS1". In a subsequent rulemaking on March 2010, EPA made a number of changes to the program, known as "RFS2". The process disclosed above may advantageously produce a renewable transportation or heating fuel that would be eligible for RINs, such as under RFS2.

Renewable fuel producers may generate RINs for fuels from feedstocks meeting the definition of renewable biomass. A fuel is considered a renewable fuel if it meets the following requirements: (i) it is a fuel that is produced from renewable biomass; and (ii) the fuel is used to replace or reduce the quantity of fossil fuel present in a transportation fuel, heating oil or jet fuel. (iii) The fuel has lifecycle GHG emissions that are at least 20 percent less than baseline lifecycle GHG emissions. (See 40 C.F.R. § 80.1401(1)).

The process described herein is believed to meet each of the foregoing legislative requirements. The higher molecular weight compounds as well as the hydrogen used in the process of producing the higher molecular weight compounds come from renewable biomass. The higher molecular weight compounds can be used to replace or reduce traditional fossil fuel based products.

Accordingly, fuel products comprising higher molecular weight compounds produced as described herein may be eligible for generation of RINs. The RINs can be generated by the producer of the higher weight molecular compounds. Acquisition of RINs by purchase or generation allows an obligated party to certify compliance with mandated renewable fuel volumes, hold the RIN for future compliance or trade it, as set out below.

Transferring RINs

The numerical information or RINs associated with the combustible fluid feedstock or renewable fuel may be provided to a government regulatory agency and a purchaser of the combustible fluid feedstock or renewable fuel for transfer to an obligated party.

Advantageously, as set out above, transfer of the RIN to an obligated party or the generation of a RIN by an obligated party may allow an obligated party to certify compliance with mandated renewable fuel volumes, or to subsequently separate the RINs and then sell or trade them. An obligated party may include, but is not limited to, any fuel production facility, including a refiner that produces gasoline or diesel fuel within the 48 contiguous states or Hawaii, or any importer that imports gasoline or diesel fuel into the 48 contiguous states or Hawaii. (See 40 C.F.R. § 80.1406).

An obligated party registers with the EPA. (See 40 C.F.R. § 80.1450(a)). The information specified for registration is set out in 40 C.F.R. § 80.76. An obligated party receives an EPA-issued identification number prior to engaging in any transaction involving RINs in accordance with 40 C.F.R. § 80.1450(a).

When a party transfers ownership of a fuel and its associated RIN, the transferor provides to the transferee, product transfer documents. (See 40 C.F.R. § 80.1453). Such documents identify the renewable fuel and any RINs (whether assigned or separated) and may include part of all of the following information, as applicable: the name and address of the transferor and transferee; the transferor's and transferee's EPA company registration numbers; the volume of renewable fuel that is being transferred; the date of the transfer; the per volume price of the RIN, if applicable; the quantity of RINs being traded; the renewable fuel type; the assignment code; the RIN generation year; the associated reason for the transaction; and any other applicable requirements.

Other information submitted to the EPA in connection with the transfer of RINs may be in the form of RIN transaction reports, listing RIN transactions, and records relating to the use of RINs for compliance including RIN activities. (See 40 C.F.R. § 80.1454).

Separating RINs

As set out above, separation of a RIN from a volume of renewable fuel means termination of the assignment of the RIN to a volume of renewable fuel. RIN separation is typically carried out by a fuel blender, importer or obligated party.

Separating RINs means that RINs are not subject to requirements to transfer them with the renewable fuel to which they are associated. That is, a separated RIN can be transferred to another party without simultaneously transferring a volume of renewable fuel to that same party. Without limitation, this allows a party to conduct RINs transactions, such as trading or selling the RIN, independent of the fuel. According to prevailing regulations, when a RIN is separated, the K code of the RIN is changed to 2.

Separation of RINs may be conducted in accordance with prevailing rules and regulations, as currently provided in 40 C.F.R. § 80.1129 and 40 C.F.R. § 80.1429. RINs generated in accordance with the invention may be separated and may also be traded.

Generation and Transfer of LCFS Credits

The process described herein can also produce fuel products that meet the low carbon fuel standards established by states within the United States or other government authorities. Transportation or heating fuels, including fuels made from crude oil derived liquid hydrocarbons, have a net GHG emission level associated with their production and this level can be compared against a standard, typically the greenhouse emission standard for gasoline set by the EPA. Due to legislative initiative and mandates, demand for renewable transportation or heating fuels with favorable net GHG emission reductions is increasing. For example, the mix of fuel that oil refineries and distributors sell into the California market can be required to meet established targets for GHG emissions. California's LCFS can require increasing reductions in the average lifecycle GHG emission of most transportation fuels. Targets can be met by trading of credits generated from the use of fuels with a lower GHG emission value than a gasoline baseline. Similar legislation has been implemented by the province of British Columbia, Canada, the United Kingdom and by the European Union and is under consideration in certain U.S. states besides California. It should be understood, however, that the invention is not limited to any particular jurisdiction in which a credit can be attained for the fuel produced in accordance with the invention.

The conversion of waste organic material into partially renewable or renewable liquid transportation or heating fuel reduces the utilization of fossil fuels. It also improves the net GHG footprint of the liquid transportation or heating fuel and provides a commercial use for waste organic material. These benefits can support the acquisition of a GHG certificate or credit that may or may not be tradable. The certificate or credit may be associated with the transportation fuel or heating fuel and represents or is proportional to the amount of lifecycle GHG emissions reduced or replaced. Methane derived from biogas has a better GHG lifecycle than that derived from natural gas.

Under RFS and LCFS, fuels are characterized by their lifecycle GHG emissions relative to baseline emissions values. For example, under RFS, advanced biofuels have the requirement that they have lifecycle GHG emissions that are at least 50 percent less than baseline lifecycle GHG emissions. To determine this measure, analyses are conducted to calculate the net GHG impact of the use of particular fuels, and are compared by reference to the use of gasoline per unit of fuel energy. Lifecycle GHG emissions evaluations generally consider GHG emissions of each: (a) the feedstock production and recovery (including if the carbon in the feedstock is of fossil origin (such as with oil or natural gas) or of atmospheric origin (such as with biomass)), direct impacts like chemical inputs, energy inputs, and emissions from the collection and recovery operations, and indirect impacts like the impact of land use changes from incremental feedstock production; (b) feedstock transport (including energy inputs, and emissions from transport); (c) fuel production (including chemical and energy inputs, emissions and byproducts from fuel production (including direct and indirect impacts)); and (d) transport and storage prior to use as a transport fuel (including chemical and energy inputs and emissions from transport and storage).

The process described herein of converting cellulosic biomass solids to a higher molecular weight compounds that can be used as a fuels product, where the process uses hydrogen generated from a portion of the reaction product reduces the lifecycle GHG emissions compared to the conventional process of using natural gas to generate hydrogen for the process. Accordingly, the fuel pathway of the products generated as described herein may be eligible for the generation of LCFS credits as a result of the GHG savings. LCFS credits would be generated in proportion to the net GHG savings generated relative to gasoline. Such credits would have associated numerical information, and could be traded by the credit generator, an intermediary, or party obligated under the LCFS.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A method comprising:
   (a) providing cellulosic biomass solids, molecular hydrogen, a slurry catalyst capable of activating molecular hydrogen, and a digestion solvent to a hydrothermal digestion unit in a hydrocatalytic reaction zone, wherein the slurry catalyst comprises at least one of Cr, Mo, W, Re, Mn, Cu, Cd, Fe, Co, Ni, Pt, Pd, Rh, Ru, Ir, Os, and any alloys thereof;
   (b) heating the cellulosic biomass solids, molecular hydrogen, a catalyst capable of activating molecular hydrogen, and digestion solvent to a temperature in a range of 110 degrees to 300 degrees C. and under a pressure in a range of 30 to 450 bar to produce a reaction product comprising an alcoholic component that comprises at least one of a monohydric alcohol, a glycol, and a triol;
   (c) providing at least a portion of the reaction product to a separation zone to recover a top fraction comprising the alcoholic component and a bottom fraction comprising compounds having a normal boiling point of greater than 350 degrees C.;
   (d) providing at least a portion of the top fraction to a further processing zone to produce a higher molecular weight compound comprising >$C_4$ hydrocarbons, wherein said further processing zone comprises a condensation reaction;
   (e) providing at least a portion of the bottom fraction to a biogas generation zone to produce a biogas comprising methane, wherein said biogas generation zone comprises anaerobic digestion of the bottom fraction;
   (f) providing at least a portion of the biogas from step (e) to a hydrogen generation zone to convert at least a portion of said biogas to molecular hydrogen; and
   (g) providing at least a portion of the molecular hydrogen from the hydrogen generation zone to said hydrothermal digestion unit in the hydrocatalytic reaction zone.

2. The method of claim 1 wherein the slurry catalyst comprises a poison-tolerant catalyst.

3. The method of claim 1 further comprising generating or receiving a renewable fuel credit for said higher molecular weight compound.

4. The method of claim 3, wherein the renewable fuel credit is a RIN or a Low Carbon Fuel Standard credit.

5. The method of claim 1 wherein the digestion solvent comprises water.

6. The method of claim 1, wherein the digestion solvent comprises an organic solvent.

7. The method of claim 1 wherein the condensation reaction takes place at a temperature in a range of 275 degrees C. and 450 degrees C.

8. The method of claim 1 wherein step (e) further comprises: providing waste organic material in addition to the bottom fraction as feed to the biogas generation zone.

9. The method of claim 1 wherein the hydrogen generation zone comprises autothermal reforming (ATR).

10. The method of claim 1 wherein the hydrogen generation zone comprises steam methane reforming (SMR).

11. The method of claim 9 wherein the hydrogen generation zone further comprises a water gas shift reaction.

12. The method of claim 10 wherein the hydrogen generation zone further comprises a water gas shift reaction.

13. A system comprising:
(a) a hydrothermal digestion unit in a hydrocatalytic reaction zone, said hydrothermal digestion unit comprising cellulosic biomass solids, molecular hydrogen, a slurry catalyst capable of activating molecular hydrogen, and a digestion solvent to, wherein the slurry catalyst comprises at least one of Cr, Mo, W, Re, Mn, Cu, Cd, Fe, Co, Ni, Pt, Pd, Rh, Ru, Ir, Os, and any alloys thereof, wherein said hydrothermal digestion unit is configured to produce a reaction product comprising an alcoholic component that comprises at least one of a monohydric alcohol, a glycol, and a triol when the cellulosic biomass solids, molecular hydrogen, a catalyst capable of activating molecular hydrogen, and digestion solvent are heated to a temperature in a range of 110 degrees to 300 degrees C. and under a pressure in a range of 30 to 450 bar;
(b) a separation zone that is in fluid communication with the hydrocatalytic zone to receive at least a portion of the reaction product, wherein the separation zone is configured to recover a top fraction comprising the alcoholic component and a bottom fraction comprising compounds having a normal boiling point of greater than 350 degrees C.;
(d) a further processing zone in fluid communication with the separation zone to receive at least a portion of the top fraction, wherein the further processing zone is configured to produce a higher molecular weight compound comprising $>C_4$ hydrocarbons, and wherein said further processing zone comprises a condensation reaction;
(e) a biogas generation zone in fluid communication with the separation zone to receive at least a portion of the bottom fraction, wherein the biogas generation zone is configured to produce a biogas comprising methane, wherein said biogas generation zone comprises anaerobic digestion of the bottom fraction; and
(f) a hydrogen generation zone in fluid communication with the biogas generation zone to receive at least a portion of the biogas, wherein the hydrogen generation zone is configured to convert at least a portion of said biogas to molecular hydrogen; and wherein the hydrogen generation zone is in fluid communication with the hydrocatalytic reaction zone to provide at least a portion of said molecular hydrogen to said hydrothermal digestion unit.

* * * * *